(12) United States Patent
Biedermann et al.

(10) Patent No.: US 8,945,194 B2
(45) Date of Patent: *Feb. 3, 2015

(54) BONE SCREW

(75) Inventors: Lutz Biedermann, VS-Villingen (DE); Jurgen Harms, Karlsruhe (DE)

(73) Assignee: Biedermann Technologies GmbH & Co. KG, Donaueschingen (DE)

( * ) Notice: Subject to any disclaimer, the term of this patent is extended or adjusted under 35 U.S.C. 154(b) by 457 days.

This patent is subject to a terminal disclaimer.

(21) Appl. No.: 13/191,299

(22) Filed: Jul. 26, 2011

(65) Prior Publication Data

US 2012/0101532 A1    Apr. 26, 2012

Related U.S. Application Data

(63) Continuation of application No. 11/319,427, filed on Dec. 29, 2005, now abandoned, which is a continuation of application No. 10/763,431, filed on Jan. 22, 2004, now Pat. No. 8,409,260, which is a continuation of application No. 10/037,698, filed on Nov. 9, 2001, now Pat. No. 6,736,820.

(30) Foreign Application Priority Data

Nov. 10, 2000  (DE) ................. 100 55 888
Dec. 27, 2000  (DE) ................. 100 65 397

(51) Int. Cl.
*A61B 17/84* (2006.01)
*A61B 17/86* (2006.01)
*A61B 17/70* (2006.01)

(52) U.S. Cl.
CPC ......... *A61B 17/7037* (2013.01); *A61B 17/7038* (2013.01); *A61B 17/7032* (2013.01)
USPC .......................... 606/305; 606/328

(58) Field of Classification Search
CPC ........... A61B 17/7038; A61B 17/7037; A61B 17/7032
USPC ......... 606/301, 305, 308, 328, 264, 266, 267, 606/246, 279, 60
See application file for complete search history.

(56) References Cited

U.S. PATENT DOCUMENTS 4,484,570 A    11/1984   Sutter
4,805,602 A    2/1989    Puno (Continued)

FOREIGN PATENT DOCUMENTS

CA    2216955       2/2004
DE    19542116 A1   5/1997

(Continued)

OTHER PUBLICATIONS

Order, dated Nov. 15, 2010, in Civil Action No. 08-1827-CKK, D.D.C. 1 page.

(Continued)

*Primary Examiner* — Pedro Philogene
(74) *Attorney, Agent, or Firm* — Christie, Parker & Hale, LLP

(57) ABSTRACT

A bone screw having a screw member possessing a threaded section and a head and a receiving part at the head end for receiving a rod to be connected to the bone screw is provided. The receiving part has on open first bore and a substantially U-shaped cross-section having two free legs provided with a thread. Furthermore, the receiving part has a second bore on the end opposite to the first bore whose diameter is greater than that of the threaded section and smaller than that of the head. On the bottom of the first bore a seat for the head is provided. In order that the screw member can be pivoted to at least one side by an enlarged angle, the edge bounding the free end of the second bore viewed relative to the axis of the first bore is of asymmetric construction.

12 Claims, 1 Drawing Sheet

(56) References Cited

U.S. PATENT DOCUMENTS

| | | |
|---|---|---|
| 4,946,458 A | 8/1990 | Harms |
| 5,057,111 A | 10/1991 | Park |
| 5,084,048 A | 1/1992 | Jacob |
| 5,129,388 A | 7/1992 | Vignaud |
| 5,133,717 A | 7/1992 | Chopin |
| 5,176,678 A | 1/1993 | Tsou |
| 5,190,543 A | 3/1993 | Schläpfer |
| 5,207,678 A | 5/1993 | Harms |
| 5,217,497 A | 6/1993 | Mehdian |
| 5,246,442 A | 9/1993 | Ashman |
| 5,253,406 A | 10/1993 | Shere |
| 5,344,422 A | 9/1994 | Frigg |
| 5,360,431 A | 11/1994 | Puno |
| 5,403,314 A | 4/1995 | Currier |
| 5,409,488 A | 4/1995 | Ulrich |
| 5,439,381 A | 8/1995 | Cohen |
| 5,443,467 A | 8/1995 | Biedermann |
| 5,466,237 A | 11/1995 | Byrd, III |
| 5,474,551 A | 12/1995 | Finn |
| 5,474,555 A | 12/1995 | Puno |
| 5,476,464 A | 12/1995 | Metz-Stavenhagen |
| 5,486,176 A | 1/1996 | Hildebrand et al. |
| 5,496,321 A | 3/1996 | Puno |
| 5,531,746 A | 7/1996 | Errico |
| 5,549,608 A | 8/1996 | Errico |
| 5,554,157 A | 9/1996 | Errico |
| 5,584,831 A | 12/1996 | McKay |
| 5,586,984 A | 12/1996 | Errico |
| 5,591,166 A | 1/1997 | Bernhardt |
| 5,609,593 A | 3/1997 | Errico |
| 5,647,873 A | 7/1997 | Errico |
| 5,669,911 A | 9/1997 | Errico |
| 5,672,176 A | 9/1997 | Biedermann |
| 5,690,630 A | 11/1997 | Errico |
| 5,725,527 A | 3/1998 | Biedermann |
| 5,725,528 A | 3/1998 | Errico |
| 5,728,098 A | 3/1998 | Sherman et al. |
| 5,733,285 A | 3/1998 | Errico |
| 5,733,286 A | 3/1998 | Errico |
| 5,735,850 A | 4/1998 | Baumgartner |
| 5,735,851 A | 4/1998 | Errico et al. |
| 5,735,852 A | 4/1998 | Amrein |
| 5,752,957 A | 5/1998 | Ralph |
| 5,797,911 A | 8/1998 | Sherman |
| 5,810,818 A | 9/1998 | Errico |
| 5,873,878 A | 2/1999 | Harms |
| 5,879,350 A | 3/1999 | Sherman |
| 5,882,350 A | 3/1999 | Ralph |
| 5,885,286 A | 3/1999 | Sherman |
| 5,891,145 A * | 4/1999 | Morrison et al. ............. 606/266 |
| 5,946,988 A | 9/1999 | Metz-Stavenhagen |
| 5,951,533 A | 9/1999 | Freeman |
| 5,954,725 A | 9/1999 | Sherman |
| 5,989,254 A * | 11/1999 | Katz ............................ 606/308 |
| 5,997,539 A | 12/1999 | Errico |
| 6,030,389 A | 2/2000 | Wagner |
| 6,053,917 A | 4/2000 | Sherman |
| 6,063,089 A | 5/2000 | Errico |
| 6,063,090 A | 5/2000 | Schläpfer |
| 6,074,391 A | 6/2000 | Metz-Stavenhagen |
| 6,077,262 A | 6/2000 | Schläpfer |
| 6,090,110 A | 7/2000 | Metz-Stavenhagen |
| 6,090,111 A | 7/2000 | Nichols |
| 6,113,601 A | 9/2000 | Tatar |
| 6,139,550 A | 10/2000 | Michelson |
| 6,280,442 B1 | 8/2001 | Barker |
| 6,299,614 B1 * | 10/2001 | Kretschmer et al. .......... 606/264 |
| 6,325,802 B1 | 12/2001 | Frigg |
| 6,355,038 B1 | 3/2002 | Pisharodi |
| RE37,665 E | 4/2002 | Ralph et al. |
| 6,443,953 B1 | 9/2002 | Perra |
| 6,471,705 B1 | 10/2002 | Biedermann |
| 6,485,491 B1 | 11/2002 | Farris |
| 6,520,963 B1 | 2/2003 | McKinley |
| 6,537,276 B2 | 3/2003 | Metz-Stavenhagen |
| 6,554,834 B1 | 4/2003 | Crozet |
| 6,736,820 B2 * | 5/2004 | Biedermann et al. ......... 606/308 |
| 6,755,830 B2 | 6/2004 | Minfelde et al. |
| 6,974,460 B2 | 12/2005 | Carbone et al. |
| 7,163,539 B2 | 1/2007 | Abdelgany et al. |
| 7,678,137 B2 | 3/2010 | Butler et al. |
| 7,785,354 B2 | 8/2010 | Biedermann et al. |
| 8,409,260 B2 * | 4/2013 | Biedermann et al. ......... 606/301 |
| 8,506,600 B2 | 8/2013 | Carbone et al. |
| 8,870,930 B2 | 10/2014 | Carbone et al. |
| 2001/0034522 A1 | 10/2001 | Frigg |
| 2002/0091386 A1 | 7/2002 | Martin |
| 2002/0183748 A1 | 12/2002 | Martin |
| 2003/0045879 A1 | 3/2003 | Minfelde et al. |
| 2003/0055426 A1 | 3/2003 | Carbone |
| 2004/0243126 A1 | 12/2004 | Carbone |
| 2005/0080420 A1 | 4/2005 | Farris |
| 2005/0283157 A1 | 12/2005 | Coates et al. |
| 2007/0043378 A1 | 2/2007 | Kumar et al. |
| 2007/0265621 A1 | 11/2007 | Matthis et al. |
| 2008/0132953 A1 | 6/2008 | Carbone et al. |

FOREIGN PATENT DOCUMENTS

| | | |
|---|---|---|
| EP | 0582857 | 2/1994 |
| EP | 0885598 A2 | 12/1996 |
| EP | 1023873 A2 | 8/2000 |
| EP | 1090595 A2 | 9/2000 |
| EP | 1273270 A1 | 1/2003 |
| FR | 2 693 365 | 1/1994 |
| FR | 2 734 471 | 11/1996 |
| FR | 2 740 674 | 5/1997 |
| FR | 2 789 293 | 8/2000 |
| FR | 2802796 | 6/2001 |
| JP | 6-142115 A | 5/1994 |
| JP | 25-10476 | 4/1996 |
| JP | 8-511189 | 11/1996 |
| JP | 11-512940 | 11/1999 |
| WO | WO-88/03781 | 6/1988 |
| WO | WO-95/25474 | 9/1995 |
| WO | WO-98/34554 | 8/1998 |
| WO | WO-99/65415 | 6/1999 |
| WO | WO-01/06940 A1 | 7/2000 |
| WO | WO-01/58370 A1 | 1/2001 |
| WO | WO-01/47425 | 7/2001 |
| ZA | 98/3429 | 11/1998 |

OTHER PUBLICATIONS

Memorandum Opinion dated Nov. 15, 2010, in Civil Action No. 08-1827-CKK, D.D.C. 33 pages.
Transcript of proceedings of Aug. 25, 2010, morning, in Civil Action No. 08-1827-CKK, D.D.C. 138 pages.
Transcript of proceedings of Aug. 25, 2010, afternoon, in Civil Action No. 08-1827-CKK, D.D.C. 36 pages.
Transcript of proceedings of Aug. 26, 2010, morning, in Civil Action No. 08-1827-CKK, D.D.C. 34 pages.
U.S. Interview Summary mailed Sep. 23, 2010, directed to U.S. Appl. No. 12/012,434, 4 pages.
Letter from Lerner, David, Littenberg, Krumholz, and Mentlik dated Jan. 14, 2011 regarding Interference No. 105,578, 2 pages.
Plaintiff Stryker Spine's Motion to Supplement the Record, filed Nov. 5, 2009, in Civil Action No. 08-1827-CKK, D.D.C. 8 pages.
Ninth Declaration of Natalie S. Morelli, dated Nov. 4, 2009, in Civil Action No. 08-1827-CKK, D.D.C. 13 pages.
Defendants' Opposition to Plaintiffs Motion to Supplement Record, filed Nov. 19, 2009, in Civil Action No. 08-1827-CKK, D.D.C. 3 pages.
Memoranda Opinion—Decision of Court on Motions for Summary Judgment dated Feb. 16, 2010, in Civil Action No. 08-1827-CKK, D.D.C. 56 pages.
Biedermann et al., U.S. Office Action, mailed Oct. 11, 2006, directed to U.S. Appl. No. 10/763,431; 8 pages.
Biedermann et al., U.S. Office Action, mailed Dec. 11, 2007, directed to U.S. Appl. No. 11/291,920; 8 pages.
Biedermann et al., U.S. Office Action, mailed Jun. 16, 2008, directed to U.S. Appl. No. 11/291,920; 6 pages.

(56) References Cited

OTHER PUBLICATIONS

Biedermann et al., U.S. Office Action, mailed Jan. 12, 2009, directed to U.S. Appl. No. 11/291,920; 7 pages.
Biedermann et al., U.S. Office Action, mailed Jul. 10, 2009, directed to U.S. Appl. No. 11/291,920; 6 pages.
Motion of Plaintiff Stryker Spine for Summary Judgment Regarding Defendant's Failure to Comply with 35 U.S.C. § 112, filed May 29, 2009; Civil Action No. 08-1827-CKK, 54 pages.
Motion of Plaintiff Stryker Spine for Summary Judgment Regarding Unpatentability of Defendants' Claims Under 35 U.S.C. §§ 102 and 103, filed on May 29, 2009; Civil Action No. 08-1827-CKK, 43 pages.
Defendant's Motion for Summary Judgment as to Each of Stryker Spine's Claims and Demands for Relief, filed on May 29, 2009; Case No. 1:08-cv-1827-CKK, 87 pages.
Defendant's Reply in Support of Their Motion for Summary Judgment as to Each of Stryker Spine's Claims and Demands for Relief, filed on Jul. 6, 2009; Case No. 1:08-cv-1827-CKK, 58 pages.
Reply of Plaintiff Stryker Spine in Further Support of Its Contingent Motion for Summary Judgment Regarding Defendant's Failure to Comply with 35 U.S.C. § 112, filed on Jul. 6, 2009; Case No. 1:08-cv-1827-CKK, 16 pages.
Reply of Plaintiff Stryker Spine in Further Support of Its Motion for Summary Judgment Regarding the PTO's Erroneous Refusal to Redefine the Interference "Count," filed on Jul. 6, 2009; Case No. 1:08-cv-1827-CKK, 30 pages.
Reply of Plaintiff Stryker Spine in Further Support of Its Contingent Motion for Summary Judgment or, in the Alternative, for Remand Regarding Unpatentability of Defendant's Claims Under 35 U.S.C. §§ 102 and 103, filed on Jul. 6, 2009; Civil Action No. 08-1827-CKK, 20 pages.
Letter from R. Wepner to B. Bretschneider and L. Dauchot dated Nov. 2, 2009, Regarding Civil Action No. 08-1827-CKK, D.D.C., 6 pages.
Expert Report of Dr. Bret Ferree in *Stryker Spine* v. *Biedermann Motech et al.*, Civil Action No. 1:08-cv-1827-CKK, D.D.C., Apr. 2, 2009.
Deposition of Dr. Bret Ferree in *Stryker Spine* v. *Biedermann Motech et al.*, Civil Action No. 1:08-cv-1827-CKK, D.D.C., Apr. 30, 2009.
Japanese Notice of Grounds of Rejection mailed on Apr. 8, 2008, directed to JP Application No. 2001/343431.
Carbone's Response to European Office Action of Dec. 20, 2005, directed to EP Application No. 02 292 236.3; 8 pages.
Carbone's Response to European Office Action of Apr. 26, 2005, directed to EP Application No. 02 292 236.3; 9 pages.
European Office Action dated Dec. 20, 2005, directed to EP Application No. 02 292 236.3; 3 pages.
Office Action dated Apr. 8, 2004, from the European Patent Office in Carbone's counterpart application.
Office Action mailed Jul. 1, 2004, issued in Carbone's U.S. Appl. No. 10/091,068.
Amendment filed on Aug. 11, 2004, in Carbone's U.S. Appl. No. 10/091,068.
European Office Action mailed on Apr. 26, 2005 relating to European Application No. 02 292 236.3-1265.
English translation of Notice of Ground of Rejection mailed Aug. 28, 2007 for patent application No. JP 343431/2001, 2 pages.
Office action for U.S. Appl. No. 10/832,214, dated Aug. 2, 2007, 10 pages.
Office action for U.S. Appl. No. 12/012,434, dated Sep. 23, 2009, 12 pages.
Amendment for U.S. Appl. No. 12/012,434, filed Mar. 19, 2010, 15 pages.
Final Rejection for U.S. Appl. No. 12/012,434, dated May 4, 2010, 20 pages.
Examiner Interview Summary for U.S. Appl. No. 12/012,434, dated Sep. 23, 2010, 4 pages.
Amendment Under 37 CFR § 1.116 for U.S. Appl. No. 12/012,434, dated Oct. 4, 2010, 12 pages.
Information Disclosure State for U.S. Appl. No. 12/012,434, dated Dec. 23, 2010, 3 pages.
Office action for U.S. Appl. No. 12/012,434, dated May 17, 2012, 11 pages.
Amendment for U.S. Appl. No. 12/012,434, dated Aug. 20, 2012, 12 pages.
Final Rejection for U.S. Appl. No. 12/012,434, dated Aug. 29, 2012, 22 pages.
Office action for U.S. Appl. No. 11/291,920, dated Dec. 11, 2007, 8 pages.
Office action for U.S. Appl. No. 11/291,920, dated Jun. 16, 2008, 6 pages.
Office action for U.S. Appl. No. 11/291,920, dated Jan. 12, 2009, 7 pages.
Office action for U.S. Appl. No. 11/291,920, dated Jul. 10, 2009, 6 pages.
Office action for U.S. Appl. No. 10/037,698, dated Jan. 29, 2003, 8 pages.
Final Rejection for U.S. Appl. No. 10/037,698, dated Jul. 15, 2003, 5 pages.
Office action for U.S. Appl. No. 11/319,427, dated Oct. 16, 2007, 8 pages.
Office action for U.S. Appl. No. 11/319,427, dated Jun. 3, 2008, 6 pages.
Final Rejection for U.S. Appl. No. 11/319,427, dated Dec. 11, 2008, 7 pages.
Office action for U.S. Appl. No. 11/319,427, dated May 28, 2009, 6 pages.
Final Rejection for U.S. Appl. No. 11/319,427, dated Dec. 22, 2009, 7 pages.
Examiner Interview Summary for U.S. Appl. No. 11/319,427, dated Apr. 16, 2010, 3 pages.
Office action for U.S. Appl. No. 11/319,427, dated Aug. 17, 2010, 4 pages.
Final Rejection for U.S. Appl. No. 11/319,427, dated Apr. 1, 2011, 11 pages.
Letter from K. Kocun to B. Bretschneider dated Jan. 14, 2011, regarding *Carbone* v. *Biedermann*, Interference No. 105,578, 2 pages.
Carbone's reply to the Office action dated Apr. 8, 2004 for European patent application No. 02292236.3, dated Oct. 14, 2004, 23 pages.
Communication under Rule 51(4) EPC for European patent application No. 02 292 236.3-1265, dated Oct. 9, 2006, 63 pages.
Expert Report of Dr. Bret Ferree in *Stryker Spine* v. *Biedermann Motech GmbH et al*, Civil Action No. 08-1827-CKK, D.D.C., Apr. 2, 2009, 32 pages.
Japanese Notice of Grounds of Rejection mailed on Apr. 8, 2008, directed to JP Application No. 2001/343431, 7 pages.
U.S. District Court, District of Columbia (Washington, DC), Civil Docket for Case #:1:08-cv-01827-CKK, 18 pages.
First Amended Complaint Pursuant to 35 U.S.C. § 146, dated Jan. 30, 2009, Document 16, *Stryker Spine* v. *Biedermann Motech GmbH*, Case 1:08-cv-01827-CKK, 38 pages.
Answer of Defendants Biedermann Motech and Depuy Spine to First Amended Complaint, dated Feb. 11, 2009, Document 23, *Stryker Spine* v. *Biedermann Motech GmbH*, Case 1:08-cv01827-CKK, 16 pages.
Motion of Plaintiff Stryker Spine for Summary Judgment Regarding The PTO's Erroneous Refusal to Redefine The Interference "Count", dated May 29, 2009, Document 31, *Stryker Spine* v. *Biedermann Motech GmbH*, Case 1:08-cv-01827-CKK, 59 pages and Documents 31-2 through 31-18.
Motion of Plaintiff Stryker Spine for Summary Judgment Regarding Defendants' Failure to Comply With 35 U.S.C. § 112, dated May 29, 2009, Document 32, *Stryker Spine* v. *Biedermann Motech GmbH*, Case 1:08-cv-01827-CKK, 54 pages and Documents 32-2 through 32-13.
Motion of Plaintiff Stryker Spine for Summary Judgment Regarding Unpatentability of Defendants' Claims Under 35 U.S.C. §§ 102 and 103, dated May 29, 2009, Document 33, *Stryker Spine* v. *Biedermann Motech GmbH*, Case 1:08-cv-01827-CKK, 43 pages and Documents 33-2 through 33-8.
Defendants' Motion for Summary Judgment As to Each of Stryker Spine's Claims and Demands For Relief, dated May 29, 2009, Document 36, *Stryker Spine* v. *Biedermann Motech GmbH*, Case.1:08-cv-01827-CKK, 87 pages and Documents 36-2 through 36-14.

(56) References Cited

OTHER PUBLICATIONS

Statement of Points and Authorities of Plaintiff Stryker Spine in Opposition to Defendants' Motion for Summary Judgment, dated Jun. 19, 2009, Document 37, *Stryker Spine* v. *Biedermann Motech GmbH*, Case 1:08-cv-01827-CKK, 47 pages and Documents 37-2 through 37-15.
Defendants' Opposition to Motion of Plaintiff Stryker Spine for Summary Judgment Regarding Unpatentability of Defendants' Claims Under 35 U.S.C. §§ 102 and 103, dated Jun. 19, 2009, Document 38, *Stryker Spine* v. *Biedermann Motech GmbH*, Case 1:08-cv-01827-CKK, 47 pages and Documents 38-2 through 38-14.
Defendants' Opposition to Plaintiff Stryker Spine's Motion for Summary Judgment Regarding Defendants Failure to Comply With 35 U.S.C. § 112, and Defendants' Supplemental Statement of Material Facts in Support of Defendants' Opposition Thereto, dated Jun. 19, 2009, Document 40, *Stryker Spine* v. *Biedermann Motech GmbH*, Case 1:08-cv-01827-CKK, 47 pages and Exhibit A, 58 pages.
*Stryker Spine* v. *Biedermann Motech GmbH, et al.*, Case No. 1:08-cv-1827-CKK, [Proposed] Order Denying Plaintiff Stryker Spine's Motion for Summary Judgment Regarding Defendants' Failure to Comply With U.S.C. § 112, filed Jun. 19, 2009, Document 40-2, 1 page.
Defendants' Opposition to Plaintiff Stryker Spine's Motion for Summary Judgment Regarding The PTO's Refusal to Redefine The Interference "Count", and Defendants' Supplemental Statement of Material Facts in Support of Defendants' Opposition Thereto, dated Jun. 19, 2009, Document 41, *Stryker Spine* v. *Biedermann Motech GmbH*, Case 1:08-cv-01827-CKK, 43 pages and Documents 41-2 through 41-3.
Reply of Plaintiff Stryker Spine in Further Support of Its Motion for Summary Judgment Regarding The PTO's Erroneous Refusal to Redefine the Interference "Count", dated Jul. 6, 2009, Document 43, *Stryker Spine* v. *Biedermann Motech GmbH*, Case 1:08-cv-01827-CKK, 30 pages and Documents 43-2 through 43-4.
Reply of Plaintiff Stryker Spine in Further Support of Its Contingent Motion for Summary Judgment Regarding Defendants' Failure to Comply With 35 U.S.C. § 112, dated Jul. 6, 2009, Document 44, *Stryker Spine* v. *Biedermann Motech GmbH*, Case 1:08-cv-01827-CKK, 16 pages and Documents 44-2 through 44-3.
Reply of Plaintiff Stryker Spine in Further Support of Its Contingent Motion for Summary Judgment or, In the Alternative, for Remand Regarding Unpatentability of Defendants' Claims Under 35 U.S.C. §§ 102 and 103, dated Jul. 6, 2009, Document 45, *Stryker Spine* v. *Biedermann Motech GmbH*, Case 1:08-cv-01827-CKK, 20 pages and Documents 45-2 through 45-5.
Defendants' Reply in Support of Their Motion for Summary Judgment As to Each of Stryker Spine's Claims and Demands for Relief, dated Jul. 6, 2009, Document 49, *Stryker Spine* v. *Biedermann Motech GmbH*, Case 1:08-cv-01827-CKK, 58 pages.
Plaintiff Stryker Spine's Motion to Supplement The Record, dated Nov. 5, 2009, Document 56, *Stryker Spine* v. *Biedermann Motech GmbH*, Case 1:08-cv-01827-CKK, 8 pages and Documents 56-2 through 56-3.
Defendants' Opposition to Plaintiffs Motion to Supplement Record, dated Nov. 19, 2009, Document 57, *Stryker Spine* v. *Biedermann Motech GmbH*, Case 1:08-cv-01827-CKK, 3 pages.
Order, dated Feb. 16, 2010, Document 59, *Stryker Spine* v. *Biedermann Motech GmbH*, Case 1:08-cv-01827-CKK, 2 pages.
Memorandum Opinion, dated Feb. 16, 2010, Document 60, *Stryker Spine* v. *Biedermann Motech GmbH*, Case 1:08-cv-01827-CKK, 56 pages.
Defendants Biedermann Motech GmbH and Depuy Spine, Inc.'s Proposed Findings of Fact and Conclusions of Law, dated Sep. 13, 2010, Document 81, *Stryker Spine* v. *Biedermann Motech GmbH*, Case 1:08-cv-01827-CKK, 34 pages.
Plaintiffs Post-Trial Proposed Findings of Fact and Conclusions of Law, dated Sep. 13, 2010, Document 82, *Stryker Spine* v. *Biedermann Motech GmbH*, Case 1:08-cv-01827-CKK, 32 pages.
Response of Defendants Biedermann Motech GmbH and Depuy Spine, Inc. To Plaintiffs Post-Trial Proposed Findings of Fact and Conclusions of Law, dated Sep. 27, 2010, Document 83, *Stryker Spine* v. *Biedermann Motech GmbH*, Case 1:08-cv-01827-CKK, 15 pages.
Response by Plaintiff Stryker Spine to Defendants' Proposed Findings of Fact and Conclusions of Law, dated Sep. 27, 2010, Document 84, *Stryker Spine* v. *Biedermann Motech GmbH*, Case 1:08-cv-01827-CKK, 25 pages and Exhibit A—9 pages.
Order, dated Nov. 15, 2010, Document 85, *Stryker Spine* v. *Biedermann Motech GmbH*, Case 1:08-cv-01827-CKK, 1 page.
Memorandum Opinion, dated Nov. 15, 2010, Document 86, *Stryker Spine* v. *Biedermann Motech GmbH*, Case 1:08-cv-01827-CKK, 33 pages.
United States Court of Appeals for the Federal Circuit, Notice of Entry of Judgment Without Opinion, Judgment Entered Jan. 12, 2012, for Case 1:08-cv-01827-CKK, Document 92, 3 pages.
Brief of Plaintiff-Appellant Stryker Spine, Appeal from the U.S. District Court for the District of Columbia in Case No. 08-CV-1827, Appeal No. 2011-1170, dated Jun. 16, 2011, 148 pages.
Brief of Defendants-Appellees Biedermann Motech GmbH and Depuy Spine, Inc., Appeal from the U.S. District Court for the District of Columbia in Case No. 08-CV-1827, Appeal No. 2011-1170, dated Aug. 19, 2011, 75 pages.
Reply Brief of Plaintiff-Appellant Stryker Spine, Appeal from the U.S. District Court for the District of Columbia in Case No. 08-CV-1827, Appeal No. 2011-1170, dated Sep. 19, 2011, 33 pages.
Board of Patent Appeals and Interferences Docket List for Interference No. 105578, 4 pages.
*John Carbone et al.* v. *Lutz Biedermann et al.*, Patent Interference No. 105,578, Order Authorizing Motions Bd.R.121, Dec. 6, 2007, 6 pages.
*John Carbone et al.* v. *Lutz Biedermann et al.*, Patent Interference No. 105,578, Request for Rehearing of Ruling That Carbone Is Not Authorized to File Motion Based on Unpatentability, Dec. 20, 2007, 9 pages.
*John Carbone et al.* v. *Lutz Biedermann et al.*, Patent Interference No. 105,578, Request for Rehearing of Ruling That Carbone Is Not Authorized to File a Motion Based on Lack of Enabling Disclosure, Dec. 20, 2007, 14 pages.
*John Carbone et al.* v. *Lutz Biedermann et al.*, Patent Interference No. 105,578, Decision—Rehearing—Bd.R. 125(c), Jan. 22, 2008, 16 pages.
*John Carbone et al.* v. *Lutz Biedermann et al.*, Patent Interference No. 105,578, Carbone Revised Substantive Motion 1 (To Redefine the Interference), Feb. 15, 2008, 30 pages.
*John Carbone et al.* v. *Lutz Biedermann et al.*, Patent Interference No. 105,578, Carbone Revised Substantive Motion 2 (For Finding of Lack of Written Description Under 35 U.S.C. § 112, First Paragraph, Pursuant to 37 CFR § 41.121(a)(1)(iii)), Feb. 21, 2008, 31 pages.
*John Carbone et al.* v. *Lutz Biedermann et al.*, Patent Interference No. 105,578, Memorandum Opinion and Order, Apr. 30, 2008, 14 pages.
*John Carbone et al.* v. *Lutz Biedermann et al.*, Patent Interference No. 105,578, Judgment, Apr. 30, 2008, 3 pages.
*John Carbone et al.* v. *Lutz Biedermann et al.*, Patent Interference No. 105,578, Request for Rehearing of Judgment Based on Denial of Carbone Revised Substantive Motion 1, May 30, 2008, 20 pages.
*John Carbone et al.* v. *Lutz Biedermann et al.*, Patent Interference No. 105,578, Decision—Rehearing—Bd.R. 125(c), Aug. 27, 2008, 11 pages.
*Stryker Spine et al.* v. *Biedermann Motech GmbH et al.*, Case: 1:08-cv-01827, Complaint Pursuant to 35 U.S.C. § 146, Oct. 24, 2008, 39 pages.
*Stryker Spine* v. *Biedermann Motech GmbH, et al.*, Civil Action No. 08-1827 (CKK), Order (Nov. 15, 2010), 1 page.
*Stryker Spine* v. *Biedermann Motech GmbH, et al.*, Civil Action No. 08-1827 (CKK), Memorandum Opinion (Nov. 15, 2010), 33 pages.
*Stryker Spine* v. *Biedermann Motech GmbH et al.*, Civil Action No. 08-1827-CKK, Notice of Appeal, Dec. 13, 2010, 3 pages.
Office action for U.S. Appl. No. 13/934,819, dated Dec. 13, 2013, 12 sheets.
Office action for U.S. Appl. No. 13/934,819 dated Apr. 17, 2014, 7 sheets.

\* cited by examiner

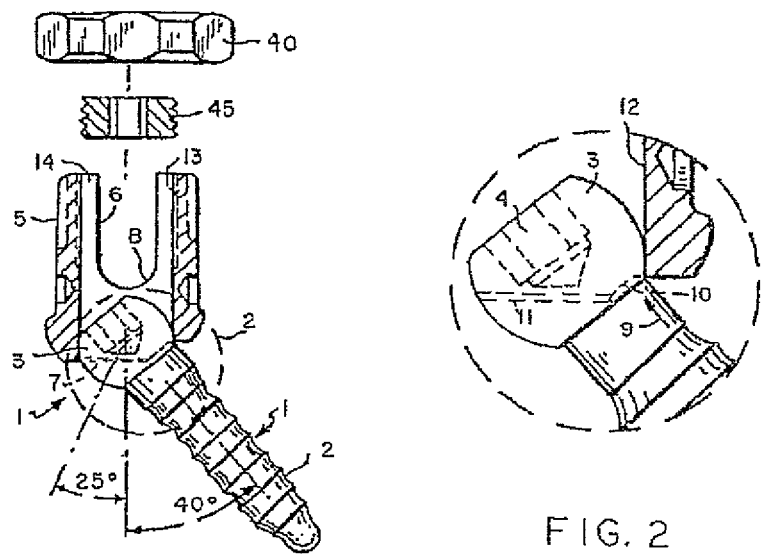
FIG. 1
FIG. 2
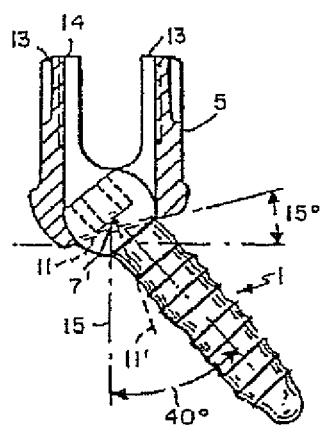
FIG. 3
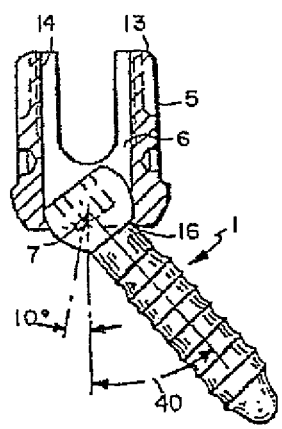
FIG. 4

BONE SCREW

REFERENCE TO RELATED APPLICATIONS

This application is a continuation of U.S. application Ser. No. 11/319,427, filed Dec. 29, 2005 now abandoned, which is a continuation of U.S. application Ser. No. 10/763,431, filed Jan. 22, 2004, now U.S. Pat. No. 8,409,260, which is a continuation of U.S. application Ser. No. 10/037,698, filed Nov. 9, 2001, now U.S. Pat. No. 6,736,820, which claims the priority of German Patent Application No. 100 65 397.9, filed Dec. 27, 2000 and German Patent Application No. 100 55 888.7, filed Nov. 10, 2000 the disclosures of which are incorporated herein by reference.

FIELD AND BACKGROUND OF THE INVENTION

The invention relates to a bone screw having a threaded section and a head and a receiving part at the head end for receiving a rod to be connected to the bone screw, the receiving part possessing an open first bore and a substantially U-shaped cross-section having two free legs provided with a thread and a second bore at the end opposite to the first bore, whose diameter is greater than that of the threaded section and smaller than that of the head and which forms the seat for the head, and a nut or screw working together with the thread.

Such a bone screw is disclosed, for example, in U.S. Pat. No. 5,672,176. In the known bone screw the head is of spherical segment-shaped construction. The bottom of the first bore adjacent to the second bore is likewise of spherical segment-shaped construction so that the spherical head lies on this spherical section. The plane going through the bounding edge is oriented at right angles to the axis of the first bore and the mid-point of the second bore coincides with the axis of the first bore. By this means it is achieved that the threaded section possessing the head is pivotable in a predetermined angle of generally up to 25° about the axis of the first bore so that even after screwing the threaded section into a vertebral segment orientation of the receiving part receiving a rod is possible. At the same time, the size of the pivot angle is limited to the extent that the second bore as a function of the diameter of the head must not exceed a certain size so that the head still has an adequate hold in the receiving part.

The use of such bone screws is something of a problem in the region of cervical vertebrae. In this case, due to the small dimensions of the cervical vertebrae, it is necessary that the screws must always be pivoted to one side and upwards, a greater degree of pivoting being necessary than is the case in the larger thoracic vertebrae and lumbar vertebrae.

SUMMARY OF THE INVENTION

The aim of the invention is to provide a bone screw which permits a larger pivot angle. This task is solved by a bone screw having a screw member that possesses a threaded section, a head and a receiving part at the head end for receiving a rod to be connected to the bone screw. The receiving part has an open first bore and a substantially U-shaped cross-section having two free legs provided with threads, a second bore at the end opposite the first bore having a diameter greater than the diameter of the threaded section and smaller than the diameter of the head, and a seat for the head and a nut or screw acting together with the thread. When viewed relative to the axis of the first bore, the edge bounding the free end of the second bore is asymmetrical.

Refinements of the invention are identified in the more detailed embodiments described below.

BRIEF DESCRIPTION OF THE DRAWINGS

Further features and practical advantages of the invention emerge from the description of exemplified embodiments with reference to the figures.

FIG. 1 depicts a side elevation of a first embodiment of the invention, partly in sectional representation.

FIG. 2 shows an enlarged detail of FIG. 1.

FIG. 3 depicts a side elevation, partly in sectional representation, of a second embodiment of the invention.

FIG. 4 depicts a corresponding representation of a further embodiment of the invention.

DETAILED DESCRIPTION OF THE INVENTION

The bone screw includes a screw member 1 having a threaded section 2 and a head 3. The head is formed in the shape of a segment of a sphere in the region adjoining the threaded section. Coaxial with the thread axis and on the end opposite to the threaded section 2 the head possesses a recess 4 for engagement with a socket screw key.

The bone screw further comprises a cylindrically constructed receiving part 5. At one end this has a first bore 6 of axially symmetrical construction. On the opposite end a second bore 7 is provided whose diameter is greater than that of the threaded section 2 and smaller than that of the head 3. On the end opposite to the second bore the first bore is open and its diameter is of such a size that the screw member 1 can be guided through the open end by its threaded section 2 going through this bore and by the head going as far as the bottom of the first bore. The bottom of the first bore is constructed as a spherically shaped region towards the open end, the radius being substantially equal to the radius of the spherical segment-shaped section of the head 3. Furthermore, the receiving part 5 has a U-shaped recess 8 arranged symmetrically relative to the center of the part whose bottom is directed towards the second bore 7 and whose two side legs 13, 14 extend to the open end directed towards the first bore 6. At the free end of the legs 13, 14 a thread for engagement with a screw member constructed as a nut 40 or screw 45 is provided. The nut or screw serves to fix a rod to be inserted into the U-shaped recess 8, it being possible for the nut or screw to act on the rod directly or via a pressure member.

In the embodiment shown in FIGS. 1 and 2, in the direction of the arrow 9, whose direction lies in a plane going through the axis of symmetry of the first bore and which is inclined to the axis of symmetry by a predetermined angle, a circular countersink 10 is made in the edge between the opening plane 11 of the second bore and the edge 12 of the first bore.

In this manner, as can be seen in the figures, it is achieved that the angle between the axis of the screw member 1 and the axis of symmetry of the first bore is substantially enlarged by comparison with the angle otherwise attainable. At the same time the seat of the screw member 1 in the receiving part is retained.

In the second embodiment shown in FIG. 3 the interior of the receiving part 5 is constructed as in the first embodiment. The opening plane 11, which bounds the second bore 7, in this embodiment is inclined at a predetermined angle α to the plane bounded by the second bore 7 so that the normal 11' to this plane 11 and the axis of symmetry of the first bore 15 enclose the angle of inclination. In the case shown this angle is 15° as an exemplified embodiment. In this version it is also achieved that the screw member 1 is pivotable in the direction shown by an angle to the axis of symmetry of the-first-bore which is substantially greater than the angle which is achievable in the usual mode of construction.

Both in the embodiment shown in FIG. 1 and the embodiment shown in FIG. 3 the countersink or chamfer is selected in such a way that in each case a small peripheral section still remains which still belongs to the spherical seat.

In a fourth embodiment which is not shown the mid-point 7' of the second bore is constructed offset to the side to a small extent, for example by 0.5 mm, relative to the axis of symmetry of the first bore. This lateral offsetting in turn produces the result that the head is held in the mounting formed by the spherically constructed bottom but a greater pivot width is achieved in a side direction.

In the exemplified embodiments described above four different approaches to a solution are presented. It is also possible to combine the individual approaches with one another; that is, for example, to combine the solution according to the first and second exemplified embodiments or one of the two with the third and/or fourth exemplified embodiment, or even all four exemplified embodiments in order to achieve, in this way, a still greater possibility for pivoting in at least one direction.

In the exemplified embodiments described above the spherical bottom of the first bore 6 is constructed in each case as an integral component of the receiving part 5. In a modified embodiment, however, the spherical bottom can also be provided either in a mounting part introduced through the first bore 6 or in a mounting part introduced through the second bore 7. The invention is then used in a corresponding manner to the end that the receiving part together with the insert piece is regarded as one member and the measures described above are taken on this piece assembled in this way.

The members forming the bone screw are preferably made of titanium.

In the embodiment shown in FIG. 4 the edge bounding the free end of the second bore viewed relative to the axis of the first bore is of symmetrical construction. The asymmetry is achieved in that the screw 1 has a recess or countersink 16 on its neck engaging on the sphere or the spherical segment so that in the manner shown in FIG. 4 as in the exemplified embodiments previously described the enlarged pivot angle can be achieved.

What is claimed is:

1. A bone fixation assembly comprising:
    a coupling element for coupling a rod to the bone fixation assembly, the coupling element having a single inner surface defining a first bore coaxial with a first longitudinal axis and a second bore communicating with the first bore; and
    an anchoring element having a first end for insertion into bone and a second end positionable within the second bore, the anchoring element being movable relative to the coupling element in at least a first direction at a first angle relative to the first longitudinal axis and in at least a second direction at a second angle relative to the first longitudinal axis, the second angle being greater than the first angle.

2. The assembly of claim 1, wherein said coupling element has an upper end and a lower end, said first bore extending from said upper end toward said lower end and said second bore extending from said lower end toward said upper end.

3. The assembly of claim 2, wherein the first end of the anchoring element is configured to project from said lower end of said coupling element.

4. The assembly of claim 2, wherein said second bore includes a seat adjacent said lower end of said coupling element, said anchoring element has a head, and wherein said seat is adapted to engage an underside of the head of said anchoring element.

5. The assembly of claim 4, wherein the underside of the head is substantially spherical, and wherein said seat has a substantially concave surface adapted to engage the spherical underside of said head.

6. The assembly of claim 5, further comprising a locking element engageable with said coupling element for locking the position of said coupling element with respect to said anchoring element.

7. The assembly of claim 4, further comprising a locking element engageable with said coupling element for locking the position of said coupling element with respect to said anchoring element, and wherein said locking element is configured to urge a stabilizing rod toward said lower end of said coupling element which in turn forces said head of said anchoring element against said seat for locking said coupling element and said anchoring element from further movement relative to one another.

8. The assembly of claim 1, wherein said coupling element has an exterior surface, an upper end and a lower end, and wherein said coupling element comprises cuts between said exterior surface and said rod-receiving openings extending from said upper end toward said lower end for minimizing the width of said coupling element.

9. The assembly of claim 1, wherein said anchoring element is a screw fastener having screw threads extending from said first end toward a second end thereof.

10. The bone fixation assembly of claim 1, further comprising a counterbore formed on the opening plane of the second bore.

11. The bone fixation assembly of claim 1, wherein an upper end of the coupling element comprises opposed spaced apart flanges defining an aperture configured to receive a rod.

12. The bone fixation assembly of claim 1, wherein the first end of the anchoring element is threaded to engage with the bone upon insertion.

* * * * *